US006623625B2

(12) United States Patent
Baird, Jr. et al.

(10) Patent No.: US 6,623,625 B2
(45) Date of Patent: Sep. 23, 2003

(54) NAPHTHENE RING OPENING OVER GROUP VIII METAL CATALYSTS CONTAINING CRACKING MODERATORS

(75) Inventors: William C. Baird, Jr., Baton Rouge, LA (US); Jingguang G. Chen, Hockessin, DE (US); Gary B. McVicker, Califon, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/897,192

(22) Filed: Jul. 2, 2001

(65) Prior Publication Data

US 2002/0040175 A1 Apr. 4, 2002

Related U.S. Application Data

(60) Provisional application No. 60/220,093, filed on Jul. 21, 2000.

(51) Int. Cl.[7] .................... C10G 35/09; B01J 23/40; B01J 23/42; B01J 23/44; B01J 23/46; C07C 5/00
(52) U.S. Cl. .................... 208/137; 208/134; 208/138; 208/133; 208/15; 585/700; 585/950; 585/940; 585/16; 502/325; 502/326; 502/327; 502/328; 502/329; 502/330; 502/331
(58) Field of Search ................. 585/700, 950; 208/133, 134, 137, 138, 15; 502/325, 326, 327, 328, 329, 330, 331

(56) References Cited

U.S. PATENT DOCUMENTS

| | | | |
|---|---|---|---|
| 3,617,485 A | 11/1971 | Kittrell | 208/59 |
| 3,617,511 A | 11/1971 | Jenkins et al. | 208/112 |
| 3,631,117 A | 12/1971 | Kovach et al. | 260/666 |
| 3,779,897 A | 12/1973 | Wrench et al. | 208/89 |
| 3,943,052 A | 3/1976 | Kmak et al. | 208/140 |
| 3,953,368 A | 4/1976 | Sinfelt | 252/466 |
| 4,018,670 A | 4/1977 | Sinfelt et al. | 208/140 |
| 4,046,673 A | 9/1977 | Paynter et al. | 208/140 |
| 4,134,823 A | 1/1979 | Bertolacini et al. | 208/65 |
| 4,140,626 A | 2/1979 | Bertolacini et al. | 208/216 |
| 4,224,192 A | 9/1980 | Foster et al. | 252/466 B |
| 4,723,963 A * | 2/1988 | Taylor | 44/57 |
| 4,783,575 A | 11/1988 | Schmidt et al. | 585/748 |
| 4,834,866 A | 5/1989 | Schmidt | 208/65 |
| 4,956,075 A | 9/1990 | Angevine et al. | 208/120 |
| 5,015,614 A * | 5/1991 | Baird, Jr. et al. | 502/250 |
| 5,026,950 A | 6/1991 | Schmidt et al. | 585/737 |
| 5,334,792 A | 8/1994 | Del Rossi et al. | 585/314 |
| 5,345,026 A | 9/1994 | Chang et al. | 585/700 |
| 5,463,155 A | 10/1995 | Galperin et al. | 585/310 |
| 5,763,731 A | 6/1998 | McVicker et al. | 585/737 |
| 5,770,042 A | 6/1998 | Galperin et al. | 208/65 |
| 5,811,624 A | 9/1998 | Hantzer et al. | 585/700 |
| 5,888,922 A | 3/1999 | Galperin | 502/163 |
| 5,906,728 A | 5/1999 | Iaccino et al. | 208/61 |
| 5,925,239 A | 7/1999 | Klein et al. | 208/213 |
| 5,928,498 A | 7/1999 | McVicker et al. | 208/213 |
| 5,935,420 A | 8/1999 | Baird, Jr. et al. | 208/213 |
| 5,993,642 A | 11/1999 | Mohr et al. | 208/46 |
| 6,221,240 B1 | 4/2001 | Klein et al. | 208/213 |

OTHER PUBLICATIONS

Schultz and co–workers (Proc. 5th Intl. Catal. Congr., North–Holland Publ. (Aidam), v.2, 1229–39, (1973)). –No month.
Egan, et al., J. Amer. Chem. Soc., 84, 1204–12 (1962). –No month.
Gault, et al., Adv. Catal., 30, 1–95, (1981). –No month.
Weitkamp, et al., in Structure and Reactivity of Modified Zeolites, Elsevier (Adam), 279–90, (1984)). –No month.
Sergienko, et al., Khim. Geol. Nauk., 2, 65–70 (1976). –No month.

* cited by examiner

*Primary Examiner*—Nadine G. Norton
(74) *Attorney, Agent, or Firm*—Gerard J. Hughes; Jeremy J. Kliebert

(57) ABSTRACT

Disclosed is a process for opening naphthenic rings of naphthenic ring-containing compounds, along with catalysts which can be used in that process. The naphthene ring opening catalyst is a catalyst which comprises at least one of a Group VIII metal selected from Ir, Pt, Pd, Rh, and Ru in an amount effective to ring open naphthene rings on naphthene ring-containing compounds, the metal being supported on a substrate comprising at least one Group IB, IIB, and IVA metal in an amount effective to moderate cracking of a naphthene ring-containing feed to form methane.

21 Claims, No Drawings

NAPHTHENE RING OPENING OVER GROUP VIII METAL CATALYSTS CONTAINING CRACKING MODERATORS

CROSS REFERENCE TO RELATED APPLICATION

This case claims benefit of U.S. Provisional Patent Application No. 60/220,093 filed Jul. 21, 2000.

FIELD OF THE INVENTION

This invention relates to a method and composition for opening naphthenic rings of naphthenic ring-containing compounds such as distillate. In particular, this invention relates to the use of a catalyst composition comprising at least one Group VIII metal supported on a material containing at least one of a Group IB, IIB, and Group IVA metal.

BACKGROUND OF THE INVENTION

There is an increasing demand for hydrocarbons boiling in the distillate boiling point range ("distillate"). Distillates typically contain paraffins, naphthenes, and aromatics. For fuel quality parameters such as cetane number, gravity and emissions, paraffins are the most desirable components, followed by naphthenes, followed by aromatics. The least desirable are multi-ring aromatic compounds. There is also an increasing demand for paraffinic solvents arising from their low toxicity and biodegradability. Consequently, it is desirable to reduce the cyclic compound content of hydrocarbon solvent blends, in general, and to convert naphthenes to paraffins, in particular. The general process of converting naphthenes to paraffins is referred to herein as ring opening.

Refinery processes that produce distillate fuels have a limited capability to produce high quality and yields of distillate fuel. For example, conventional hydrogenation processes saturate aromatic rings to form naphthenes, thereby increasing the cetane number and increasing the API gravity (i.e., lowering the density). However, single ring and multi-ring naphthenes have generally lower cetane values and are denser than paraffins having substantially the same number of carbon atoms. The greater density of naphthenes results in reduced volume of the distillate fuel blend relative to compositions containing similar concentrations of paraffins instead of naphthenes. Hydrocracking catalysts, typically composed of hydrogenation metals supported on acidic supports, are also effective for aromatics hydrogenation and for ring opening by cracking. However, cracking tends to make lower boiling point products, including a significant quantity of undesired gas by-products, which lowers the overall boiling range and limits the volume of final distillate product. In fact, hydrocracking products generally do not contain more distillate boiling range paraffins than the hydrocracking feeds. Moreover, a significant portion of the total paraffin concentration in the final product of conventional hydrocracking processes, including gas by-products, are relatively low molecular weight compounds that are outside the distillate boiling range. Thus, the apparent increase in distillate boiling range paraffins and improved distillate fuel quality may result primarily from a combination of the hydrogenation of aromatics and a concentration of paraffins in a reduced volume of distillate product, the latter arising from removing the undesired paraffin gas by-product, i.e., the low boiling point paraffin gas components.

There is, therefore, a need for selective ring opening processes for converting single and multi-ring aromatic species, including alkyl functionalized derivatives thereof, into distillate boiling range paraffins without producing a significant amount of undesirable low boiling point saturated species. Selectivity for ring opening is related to the propensity for cleavage of a ring bond which results in product molecules having an equivalent number of carbon atoms and at least one less ring than the original molecule, rather than cleavage of a bond which results in a product molecule having fewer carbons than the original molecule. A perfectly selective ring opening process would give only ring bond cleavage to produce molecules having an equivalent number of carbon atoms and at least one less ring than the original molecule. For example, from a hydrocarbon stream containing only single ring naphthenes of n number of carbon atoms, the product from perfect ring opening selectivity would contain only paraffins of n number of carbon atoms. Thus, the greater number of product molecules from a ring opening process having an equivalent number of carbon atoms and at least one less ring than the original molecule, the greater the selectivity for ring opening.

Conventional ring opening processes use a wide range of catalysts, including bifunctional metal hydrogenation-acidic catalysts. Distillate quality may be improved by controlling paring isomerizations and subsequent dealkylations in order to limit the number of lower cetane, highly branched paraffins that may result from conventional ring opening.

Some conventional processes for forming an improved distillate employ Ir catalysts for opening naphthene ring compounds. Even though distillates such as diesel, jet fuel and heating oil contain at least about 20 vol. %, generally about 20 to about 40 vol. % of $C_6$ naphthenes, the conventional processes open $C_6$ naphthenes at low rates, if at all. This problem is exacerbated with hydrotreated distillates because they have a still greater concentration of $C_6$ naphthenes. In order to overcome this problem of poor opening of $C_6$ naphthene rings, U.S. Pat. No. 5,763,731 teaches using Ir along with at least one acidic co-catalyst, preferably a zeolite, to isomerize the $C_6$ naphthene rings to $C_5$ rings. However, since the resulting $C_5$ ring structure will typically bear increased numbers of substituents, such as alkyl groups, this approach increases the volume of branched paraffins upon ring opening. In addition, the presence of an acidic co-catalyst has a tendency to isomerize any naturally present linear paraffin into a branched paraffin, often resulting in a ring-opened product that has an undesirably high concentration of branched paraffins. Moreover, the process results in increased light saturated gas production, particularly at high temperature.

Another conventional process, set forth in U.S. Pat. No. 5,811,624, uses Ir along with at least certain transition metals for isomerizing $C_6$ naphthene rings to $C_5$ naphthene rings, with the Ir component being particularly effective for opening the $C_5$ naphthene rings. However, the product contains a significant concentration of branched paraffins, which leads to a lower product cetane number. There is still a need, therefore, for a ring opening process and catalyst which provide a much higher degree of linear paraffin functionality in the ring opened product, and at the same time, provide a greater volume of product in the distillate range.

SUMMARY OF THE INVENTION

In one embodiment, a ring opening catalyst and process are provided to form a reduced number of ring structures in the product stream, minimize dealkylation of any pendant substituents optionally present on the ring structure, and increase volume of the product. In particular, the invention is beneficial in that it provides a relatively high content of more linear paraffins in the product. In one embodiment, the invention provides paraffins having a more linear (i.e., less branchy) character than conventional methods and catalysts using feeds containing both $C_5$ and $C_6$ naphthene ring compositions having tertiary carbons. The ring-opened product provides a diesel or jet fuel product, which has a high degree of linear and less branched paraffins, particularly one having a high degree of linear and less branched $C_9^+$ paraffins. This translates to a fuel product which is high in cetane number, a highly sought after fuel quality.

Specifically, a highly selective catalyst, which is provided for converting naphthene feed into paraffin product containing a substantial quantity of linear and less branched paraffins, with a relatively low methane yield. The invention is particularly beneficial in converting a naphthene feed containing a $C_6$ naphthene ring-containing composition, wherein the $C_6$ ring contains at least one tertiary carbon, to a product containing a substantial quantity of linear and less branched paraffin compounds.

In one embodiment there is provided a catalyst which comprises a Group VIII metal selected from Ir, Pt, Pd, Rh, Ru, and combinations thereof, in an amount effective to ring open a naphthene ring of a naphthene ring-containing compound, the metal being supported on a substrate comprising at least one of a Group IB, IIB, and IVA metal in an amount effective to moderate cracking of a naphthene ring-containing feed to form methane. Desirably, the Group VIII metal is present in a range of about 0.01 to about 10.0 wt. %. In a preferred embodiment, the Group VIII metal is present in a range of about 0.1 to about 7.0 wt. %, more preferably in a range of about 0.3 to about 6.0 wt. %, and most preferably in a range of about 0.3 to about 5.0 wt. %.

In another preferred embodiment, the substrate contains a refractory inorganic oxide. Preferably, the refractory inorganic oxide is at least one of alumina, silica, zirconia, titania, chromia, zinc oxide, magnesia, thoria, boria, silica-alumina, silica-magnesia, chromia-alumina, alumina-boria, silica-zirconia. More preferably, the substrate is alumina.

The Group IB metal is preferably at least one of Cu, Ag, and Au. The Group IIB metal is preferably Zn. The Group IVA metal is preferably selected from Ge, Sn, Pb. Therefore, the metal is preferably selected from Cu, Ag, Au, Zn, Ge, Sn, Pb, and combinations thereof.

Desirably, the total amount of cracking moderator (i.e., the total amount of any Group IB, IIB, and IVA metal present) in the catalyst ranges from about 0.01 to about 5.0 wt. %. Preferably, the cracking moderator is present in a range of about 0.01 to about 3.0 wt. %, more preferably in a range of about 0.01 to about 2.0 wt. %, and most preferably in a range of about 0.01 to about 1.0 wt. %.

In a more preferred embodiment, the Group VIII metal is Ir and the cracking moderator is Cu or Sn. In an alternative embodiment, the Group VIII metal is Pt and the cracking moderator is Cu or Sn. In yet another embodiment, the Group VIII metal is a combination of Pt and Ir and the cracking moderator is Sn.

A process is also provided for opening naphthene rings of naphthene ring-containing compounds in a feed stream. The process comprises providing a naphthene ring-containing feed stream, and contacting the naphthene ring-containing feed stream with a catalyst of the invention. In a desirable embodiment, the method further comprises ring opening naphthene rings having at least one tertiary carbon site at the tertiary carbon site, thereby forming a ring opened product having increased linear paraffin functionality relative to that of the feed stream.

The method may also include recovering the ring opened product. The ring opened product may be used directly, for example, as a diesel fuel, jet fuel, gas oil, and heating oil, and it may also be blended with other petroleum streams for use, for example, as a diesel fuel, jet fuel, gas oil, and heating oil. Preferably, the ring opened product is blended with a petroleum stream having a boiling point of about 175° C. to about 600° C., wherein the blend has a cetane number of at least about 40.

Ring opening may be carried out at a temperature ranging from about 150° C. to about 400° C.; a total pressure ranging from about 100 to about 3,000 psig; a space velocity ranging from about 0.1 to about 10 V/V/Hr; and a hydrogen treat gas rate ranging from about 200 to about 10,000 standard cubic feet per barrel (SCF/B). The feed stream in the ring opening process is preferably a petroleum feed stream which has a boiling point of from about 175° C. to about 600° C., more preferably about 175 to about 500° C.

Preferably, the ring opening catalysts of the invention are capable of ring opening at least about 20% of an amount of 1,2-dimethylcyclohexane at the tertiary carbon site. More preferably, the ring opening catalysts are capable of ring opening between about 30% and about 40% of the amount of 1,2-dimethylcyclohexane at the tertiary carbon site.

The invention further relates to a product made by the ring opening process. The product is higher in linear paraffin functionality compared to conventional ring opened products.

DETAILED DESCRIPTION OF THE INVENTION

The invention is based in part on the discovery of ring opening catalyst compositions useful in processes for forming high cetane number distillate having a desirable concentration of compounds, which have a high degree of linear paraffin functionality. Increasing ring opening process severity, for example, by increasing reaction temperature, is known to increase the yield of ring opened product. However, as severity increases, the yield from undesirable side reactions also increases, leading to an undesirable increase in the yield of light saturated products such as methane. This invention relates in part to the suppression of such side reactions by using ring opening catalysts containing at least one Group VIII metal and at least one of a Group IB, IIB, and IVA metal. In a preferred embodiment, the catalyst compositions are useful for opening rings at tertiary carbon sites in naphthene or naphthenic ring-containing distillates in order to form products with a high degree of linear paraffin functionality. The compositions are especially effective in opening compounds containing $C_5$ and $C_6$ naphthene rings bearing at least one tertiary carbon.

As defined herein, compounds having a high degree of linear paraffin functionality have fewer paraffin (i.e., alkyl) side chains and longer paraffin substituents. According to this definition, linear paraffins, particularly $C_{10}$–$C_{20}$ linear paraffins, are the most highly desirable compounds for use as a diesel or jet fuel product, though other compounds having a relatively high degree of linear paraffin functionality are also acceptable. For example, a cycloalkane ring compound having a single, linear alkyl side chain has relatively high paraffin functionality compared to a cycloalkane ring having multiple side chains. By the same definition, an aromatic ring compound having a single, linear alkyl side chain has a relatively high linear paraffin functionality compared to an aromatic ring compound having multiple side chains.

As defined herein, a tertiary carbon (3° carbon) is the site of location of a substituent group on a naphthenic ring compound. Tertiary carbons are represented by such structural features, for example, as —CH(R)—CH$_2$— and —CH(R)—CH(R)—where R is a carbon-containing chain, preferably a C$_1$–C$_{10}$ carbon-containing chain.

Opening the ring structure of naphthenic ring compounds at the tertiary carbon site, known as tertiary bond cleavage, is particularly desirable for C$_6$ naphthenic rings. Tertiary bond cleavage is advantageous because isomerization of the C$_6$ rings to C$_5$ rings is abated so that the ring-opened product will have a high degree of linear paraffin functionality.

As used herein, a naphthene or a naphthenic ring-containing composition refers to a cycloalkane or a composition containing at least one cycloalkane ring in its structure. For example, the term can refer to either a C$_5$ or C$_6$ ring-membered cycloparaffin. The cycloparaffin can also include various side chains, particularly one or more alkyl side chains of 1–10 carbons. In addition the cycloparaffin can be attached or fused to other ring structures, forming two or three membered ring compounds. The additional ring members can be saturated or unsaturated, as long as at least one ring of the complete structure contains a tertiary carbon. Examples of two and three membered ring structures that can contain a tertiary carbon include saturated or partially saturated naphthalenes, indenes, fluorenes, phenanthrenes, anthracenes, acenaphthalenes, and biphenylenes.

A feedstream which is to be ring opened will typically contain a mix of hydrocarbons having one or more of the naphthene ring-containing compositions, and the naphthene ring-containing compositions preferably contain at least one alkyl substituent. Preferably, the feedstream will comprise at least 5 vol. % of at least one naphthenic ring-containing compound more preferably at least 25 wt. %, most preferably at least 50 wt. %. Typically the feedstream will comprise from about 5 to about 85 vol. % of at least one naphthenic ring-containing compound, based on the volume of the feedstream.

In a more preferred embodiment, the hydrocarbon containing the naphthene ring compositions that are to be opened will include C$_5$ and C$_6$ naphthene ring compounds that do not include additional ring members. Non-limiting examples of these compounds include methylcyclopentanes, ethylcyclopentanes, propylcyclopentanes, butylcyclopentanes, pentylcyclopentanes, methylcyclohexanes, ethylcyclohexanes, propylcyclohexanes, butylcyclohexanes, and pentylcyclohexanes. Preferably; the C$_5$ and C$_6$ ring naphthene ring compounds contain alkyl substituents.

Naphthenic ring-containing compounds are found in a wide variety of hydrocarbon feeds, such as petroleum streams boiling in the distillate range. These streams will typically include a variety of chemical compounds, including multi-ring compositions. Preferably, this invention uses a petroleum feed stream having a boiling point ranging from about 175° C. to about 600° C. Examples of such a feed stream include diesel fuel, jet fuel, heating oil, gas oil, and light cycle oil. Gas oil includes vacuum gas oil boiling in the range from about 340° C. to about 565° C., which is typically derived from vacuum distillation of crude oil, or it can be obtained by conversion of products such as coker gas oil or heavy cat cycle oil. Other feed streams can also be used if appropriately pre-treated. These streams include chemical feed streams and lube streams.

In particular, the process provides Group VIII-based ring opening catalysts which exhibit desirable tertiary bond cleavage, and which moderate or suppress undesirable methane formation. This moderation of methane formation leads to the formation of higher cetane number paraffinic species in the reaction product. The Group VIII-based ring opening catalysts incorporate an effective amount of hydrogenolysis suppressors (i.e., cracking suppressors) such as the Group IB, IIB, and IVA metals in order to form the higher cetane paraffin product. An effective amount in this context is the amount of Group IB, IIB, and IVA metal to suppress undesirable hydrogenolysis side reactions. As undesirable hydrogenolysis products may be readily identified by conventional methods, the effective amount of Group IB, IIB, and IVA metal may be readily determined.

Polymetallic catalysts such as Group VIII-Group IB, Group VIII-Group IIB, and Group VIII-Group IVA catalysts are preferred as effective ring opening catalysts. The catalysts exhibit improved cracking patterns at severe process conditions, and in particularly preferred embodiments, the formation of less branched paraffins.

In one embodiment, the naphthene ring opening catalysts of this invention comprise at least one of the Group VIII metals, preferably at least one of Ir, Pt, Pd, Ru, and Rh, supported on a material (i.e., a substrate) containing the Group IB metals, such as Cu, Ag, Au, the Group IIB metals, such as Zn, or the Group IVA metals, such as Sn, all of which can be used alone or in mixtures thereof. Preferred Group VIII metals are Ir, Pt, and Ru, more preferred Group VIII metals are Ir and Pt. Particularly preferred cracking moderators are Cu, Sn, or Zn, all of which can be used alone or in mixtures thereof.

The Group VIII metal (or metals) is present in the catalyst in an amount effective to ring open naphthene rings on naphthene ring-containing compounds. The total loading of the Group VIII metal catalyst components can range from about 0.01 to about 10 wt. %. Total loadings of about 0.1 to about 7.0 wt. % are preferred; loadings of about 0.3 to about 6.0 wt. % are more preferred; and loadings of about 0.3 to about 5.0 wt. % are most preferred.

In a preferred embodiment, the catalyst preferably comprises Ir in combination with at least one other or "second" Group VIII metal selected from Pt, Ru, and Rh. In a preferred embodiment, the other Group VIII metal is Pt. The Ir and the other Group VIII metal are present in an amount effective for opening a naphthene ring at a tertiary carbon site. Desirably, Ir is present in a range of about 0.1 to about 2.0 wt. %, preferably in a range of about 0.3 to about 1.5 wt. %, more preferably in a range of about 0.5 to about 1.2 wt. %, and most preferably in a range of about 0.5 to about 1.0 wt. %, based on the weight of the ring opening catalyst. It is also desirable that the second Group VIII metal be present in a range of about 0.001 to about 2.0 wt. %, preferably in a range of about 0.005 to about 1.5 wt. %, more preferably in a range of about 0.007 to about 1.3 wt. %, and most preferably in a range of about 0.01 to about 1.0 wt. %, based on the weight of the ring opening catalyst.

The cracking moderator is present in an amount effective to moderate cracking of a naphthene ring-containing feed to form methane. Desirably, the cracking moderator is also present in an amount effective for enhancing ring opening of the naphthene ring-containing compounds which contain a tertiary carbon site. The total loading of the Group IB, IIB or IVA metals (i.e., the total cracking moderator loading) can range from about 0.01 to about 5.0 wt. %, based on the total weight of the catalyst. Total loadings of about 0.01 to about 3.0 wt. % are preferred; loadings of about 0.01 to about 2.0 wt. % are more preferred; and loadings of about 0.01 to about 1.0 wt. % are most preferred. Preferred, but not limiting, catalyst compositions within these limits include Ir—Cu, Ir—Sn, Pt—Ir—Sn, Pt—Cu, and Pt—Sn.

The naphthene ring opening catalysts can be supported on conventional refractory supports. Particularly desirable supports are refractory inorganic oxides. Non-limiting examples of refractory inorganic oxides include alumina, silica, zirconia, titania, chromia, zinc oxide, magnesia, thoria, boria, silica-alumina, silica-magnesia, chromia-alumina, alumina-boria, silica-zirconia, and combinations thereof. Low-acidity support materials such as alumina are preferred.

In a particularly preferred embodiment, the alumina support is prepared by digesting high purity alumina hydrate powder in a weak organic acid, thereby forming an alumina sol which is then spray-dried by a conventional spray-drying technique to produce the alumina hydrate powder. If the alumina hydrate powder is not of appropriate particle size, it can be ground by any conventional grinding means for reducing the particle size of refractory powders. The alumina hydrate powder is then blended with an effective amount of water, or sol, to form a paste of sufficient consistency for extrusion. The alumina paste is then extruded into an appropriate shape, such as pellets, dried and calcined at temperatures from about 400° C. to about 650° C. The metals can be introduced in any one or more of the above process steps. A more complete description of this process is described in U.S. Pat. No. 5,015,614, which is incorporated herein by reference.

In one embodiment of the invention, the Group VIII metal and the cracking moderator may be supported on a modified substrate. The modified substrate may be prepared by incorporating therein an effective amount of modifier. The modifier is such that, when used in an effective amount, it contributes to the resulting ring opening catalyst an improved overall selectivity with respect to linear and less branched paraffin yield, with simultaneous suppression of isomerization reactions when compared to an identical catalyst not containing such modifiers. In other words, the term "effective amount of modifier" as used herein refers to the concentration range of modifier which, when used in a ring opening process, will improve the selectivity to linear and less branched paraffin formation from naphthene rings and reduce isomerization of linear paraffins. Preferred elements that can be incorporated as modifiers into the substrate for the purposes of this invention include Cs, Mg, Ca, and Ba. Ca, Mg, and Ba are more preferred, with Mg being most preferred.

Generally, the modifier concentration in the ring opening catalyst will be at least about 0.1 to about 50 wt. %. Preferably, the modifier concentration in the ring opening catalyst will be about 0.5 to about 40 wt. %, more preferably about 1 to about 30 wt. %, and most preferably about 2 to about 25 wt. %. The modifier component can be incorporated into the substrate during any stage of production.

The modifier is preferably added to the substrate material as aqueous solutions of their common salts, preferably nitrates, nitrites, oxides, hydroxides, halides, carboxylates, and the like using either incipient wetness or absorption from solution techniques. Incipient wetness is a preferred procedure. Although the modifier can be added to the substrate material after extrusion of the substrate, it is preferable to add modifier prior to extrusion to ensure homogeneity of the modifier elements throughout the substrate.

The modified substrate compositions of this invention are also characterized as having: (i) a surface area greater than about 50 $m^2/g$, preferably from about 100 to about 700 $m^2$ g, and more preferably from about 100 to about 300 $m^2/g$; (ii) a bulk density from about 0.3 to about 1 g/ml, preferably from about 0.4 to about 0.8 g/ml; (iii) an average pore volume from about 0.2 to about 1.1 ml/g, preferably from about 0.3 to about 0.8 ml/g; and (iv) an average pore diameter from about 30 to about 300 Angstroms.

The addition of the Group VIII metal(s) and the cracking moderator (i.e., the Group IB, IIB, and IVA metals) to the support material may be accomplished by conventional techniques. Preferred techniques include incipient wetness impregnation and absorption from excess aqueous solution. Alternatively, the metals may be incorporated into the support material during its preparation as disclosed and claimed in U.S. Pat. No. 4,963,249, the description of which is incorporated herein by reference.

The Group IB, IIB, and IVA metals may be added in metal precursor form, such as in the form of metal halides, nitrates, nitrites, oxides, hydroxides, carboxylates, and the like. This method of preparation is described in detail in U.S. Pat. No. 4,231,898, the description of which is incorporated herein by reference.

The Group VIII metal(s) may also be added in precursor form. Suitable metal precursors are the halides, the halometallic acids, nitrates, nitrites, amine halo complexes, amine nitrate complexes, and amine nitrite complexes.

Incipient wetness is a particularly desirable method for incorporating the desired level of Group VIII metal into the modified substrate. The metal is preferably dissolved in solution, desirably in precursor form. Metal deposition from organic solvents may also be practiced using organometallic complexes such acetylacetonates, carbonyls and the like. Once the metal complexes have been impregnated, they are decomposed by thermal treatment in an air, hydrogen, or inert atmosphere. This can be accomplished by conventional heating or by the application of microwave or ultrasonic radiation. The decomposition of the metal complex will leave the Group VIII metal impregnated in the substrate.

The naphthene ring opening catalysts may be activated according to conventional methods. For example, they may be activated by drying in air at a temperature ranging from about ambient temperature to about 300° C. for about 4 to about 24 hours and reducing in-flowing hydrogen, preferably in situ, at a temperature ranging from about 200° C. to about 600° C. for about 0.5 to about 24 hours. Drying at temperatures below 200° C. and reducing at about 350° C. to about 500° C. for about 4 hours are preferred.

As discussed, the preferred ring opening catalyst compositions are useful in processes for forming high cetane number distillate having a desirable concentration of compounds which have a high degree of linear paraffin functionality. To convert naphthene compounds to paraffins, a catalytically effective amount of at least one catalyst of this invention is contacted with an appropriate feed stream under catalytic ring opening conditions. Preferred conditions are such that the $C_5$ and $C_6$ rings of the naphthene compounds are opened when contacted with the catalyst. While conventional process conditions may be employed, preferred process conditions include a temperature ranging from about 150° C. to about 400° C., preferably from about 225° C. to about 350° C., a total pressure ranging from about 100 to about 3,000 psig, preferably from about 100 to about 2,200 psig; more preferably about 100 to about 1,500 psig, a liquid hourly space velocity ranging from about 0.1 to about 10 V/V/Hr, preferably from about 0.5 to about 5 V/V/Hr, and a hydrogen treat gas rate ranging from about 200 to about 10,000 SCF/B, preferably about 500 to about 5000 SCF/B. SCF/B means standard cubic feet per barrel, and V/V/Hr means volume of feed per volume of catalyst per hour.

Conventional ring opening reactors may be used in the ring opening process of this invention. A fixed bed reactor system wherein the feedstock is passed over one or more stationary beds of catalyst is preferred. Multiple reactors may be used in either series or parallel configurations.

Hydrogen gas (i.e., a hydrogen-containing treat gas) conducted to the reaction process may flow over the catalyst either in a direction co-current or countercurrent with the feedstock. Hydrogen is supplied to saturate the carbons where ring opening occurs, and it is preferably supplied in stoichiometric excess. In one embodiment, the reactor effluent is passed to a separation zone where hydrogen that has not been consumed in the reaction process is separated and suitably recycled to the reaction zone together with make-up hydrogen as needed. In another embodiment, the treat gas is employed in a "once-through" arrangement and is therefore not recycled.

Countercurrent reactors incorporating the catalyst are a preferred embodiment, since properly constructed countercurrent reactors can provide better contacting of reactants and treat gas. They are particularly beneficial in maintaining a low $H_2S$ partial pressure. Such a reactor is disclosed in U.S. Pat. No. 5,942,197, the description of which is incorporated herein by reference. This preferred design is less susceptible to flooding than conventional countercurrent reactors because it incorporates passageways to bypass one or more catalyst beds. Bypass of at least a portion of the hydrogen treat gas is designed to occur when the pressure differential across the catalyst bed increases to a predefined threshold correlating to a near-flood condition. When gas bypasses the catalyst bed, the pressure differential across the catalyst bed decreases to permit the downward flow of liquid. When the pressure differential falls below a predefined level, the bypassing of gas is automatically stopped.

It is preferred that the feed streams be hydrotreated prior to ring opening to reduce sulfur content to low levels, preferably less than about 10 ppm, more preferably less than about 1 ppm, most preferably less than about 0.1 ppm. This is particularly desirable when high sulfur feeds are used in the ring opening process, since the ring opening catalysts are sensitive to high sulfur content.

Hydrotreating to reduce sulfur is referred to herein as hydrodesulfurization. Conventional hydrodesulfurization catalysts may be used to reduce the sulfur content of feed containing sulfur compounds to the preferred levels.

Non-limiting examples of conventional hydrodesulfurization catalysts which may be used to reduce the sulfur content of the feed include catalysts which comprise a Group VI metal with one or more Group VIII metals as promoters, the metals being on a refractory support. Conventional hydrodesulfurization processes are conducted at pressures ranging from about 50 to about 2000 psig, preferably from about 100 to about 1500 psig, liquid hourly space velocities ranging from about 0.2 to about 6 V/V/Hr, and a hydrogen gas rate of about 200 to about 5000 SCF/B (standard cubic feet per barrel). The liquid hourly space velocity is based on the volume of feed per volume of catalyst per hour, i.e., V/V/Hr.

Sulfur sorbents, including regenerable sulfur sorbents, may also be used to reduce the sulfur content of the feed. These materials are capable of removing the easy sulfur compounds, particularly hydrogen sulfide, under relatively mild sulfur removing conditions. Examples of sulfur sorbents include metal oxides. These systems are disclosed in U.S. Pat. Nos. 5,928,498; 5,925,239; 5,935,420; 4,003,823; 4,007,109; 4,087,348; 4,087,349; 4,119,528; and 4,127,470 all of which are incorporated by reference herein.

If significant aromatic compounds are present in the feed stream, it is desirable to saturate them. It is preferred that the feedstock contain less than about 20 wt. % total aromatic compounds, preferably less than about 15 wt. %, more preferably less than about 10 wt. %.

The aromatics saturation (ASAT) process may be performed in one or a series of reactors either before or after the ring opening process, since either mode will generally result in a product having increased cetane number due to the lowering of the aromatic content. Saturation of aromatics in the feed is preferred, however, prior to the ring opening process. This is because saturation of aromatics tends to result in the formation of additional naphthenes, providing additional material that can ultimately be converted using the catalyst of this invention to form compounds having a higher degree of linear paraffin functionality. In another preferred embodiment, a hydrodesulfurization reactor will be placed in front of the aromatics saturation reactor so that the catalyst in the aromatics saturation reactor will contact low sulfur feedstock.

Any conventional aromatic saturation process may be used to hydrogenate the aromatic rings of the aromatic compounds in connection with one embodiment. Typical conditions for saturating aromatics-containing feedstocks include temperatures from about 150° C. to about 400° C., pressures from about 100 to about 2000 psig, space velocities from about 0.4 to 6 V/V/Hr, and hydrogen gas rates from about 200 to about 6000 standard cubic feet per barrel (SCF/B). Lower temperatures are found to be most desirable for the hydrogenation or saturation reactions since nonselective cracking reactions thereby are minimized. Selective saturation of the aromatics results in a saturated intermediate from the hydrogenation zone usually containing less than 15 weight % total aromatics.

Ring opening may also be practiced in a variety of stacked or mixed bed configurations along with aromatics saturation and sulfur removal. The stacked and mixed beds can occupy a single reactor or multiple reactors, and may take place in either co-current or countercurrent mode. The stacking of fixed beds of catalyst refers to the sequence of beds disposed with respect to the direction of flow of the liquid phase reactants. In a single reactor, such beds would be vertically disposed from top to bottom. In a series of reaction vessels the sequence is defined by the flow of the liquid phase.

A reactor may, for example, be loaded to have stacked layers of a sulfur reducing catalyst (e.g., a hydrodesulfurization (HDS) catalyst); a sulfur sorbent (sorbent); an aromatics saturation (ASAT) catalyst; and/or a ring opening (RO) catalyst. Specific examples of stacked catalyst arrangements include: HDS/ASAT/sorbent/RO; HDS/RO/ASAT; sorbent/ASAT/RO; and HDS/sorbent/ASAT/RO. Preferred mixed bed catalyst arrangements include: RO+ASAT; sorbent+RO; sorbent+ASAT+RO; and sorbent+HDS+RO. Conditions favoring the ring opening function are preferred.

The ring opened product may be recovered after the final processing step, i.e., after ring opening, after an optional ASAT final step, or after any further optional treatment step, according to conventional methods. The recovered product may be used directly, for example, as a diesel fuel, jet fuel, gas oil, and heating oil, and it can be blended with other petroleum products and used, for example, as a diesel fuel, jet fuel, gas oil, and heating oil. When blended, it is preferred that the ring opened product be blended with a petroleum stream having a boiling point of about 175° C. to about 600° C., wherein the blend has a cetane number of at least about 40.

The Periodic Table of the Elements referred to herein appears on the inside cover page of the Merck Index, 12th Ed., Merck & Co., 1996.

This invention will be better understood with reference to the following examples, which are intended to illustrate specific embodiments within the overall scope of the invention as claimed.

General Experimental

In the examples, tertiary bond cleavage (%) is determined by dividing the wt. % yield of ring opened products involving tertiary centers by the total wt. % yield of all ring opened products and multiplying by 100. For example, methylcyclohexane ("MCH") tertiary bond cleavage in the examples= 100×(wt. % n-heptane/(wt. % n-heptane+wt. % isoheptanes)); for 1,2-dimethylcyclohexane ("1,2 DMCH") tertiary bond cleavage=100×((wt. % n-octane+wt. % 3-methylheptane)/(wt. % n-octane+wt. % 3-methylheptane+ wt. % 2,3-dimtehylhexane+wt. % 3,4-dimethylhexane)). Metal loadings are in weight percent, based on the weight of the catalyst. For example, a catalyst of 0.9 wt. % Ir and 0.9 wt. % Pt, based on the weight of the catalyst is written as 0.9 Ir-0.9Pt.

EXAMPLE 1 (COMPARATIVE)

A 0.9 wt. % Ir/$Al_2O_3$ ring opening catalyst was prepared by impregnating 50 g of reforming grade alumina with 28 ml of a chloroiridic stock solution containing 16 mg Ir/ml. The catalyst was dried at 120° C. for 24 hr and reduced at 450° C. for 3 hr. The catalyst was used to ring open methylcyclohexane under the following conditions: 300° C., 200 psig, 10 W/H/W, $H_2$/Oil=6. The results are found in the Table 1.

EXAMPLE 2

A 0.9Ir-0.03Cu/$Al_2O_3$ catalyst was prepared as in Example 1 with copper nitrate being added to the Ir solution. The catalyst was dried at 120° C. for 24 hr and reduced at 450° C. for 3 hr. The catalyst was used to ring open methylcyclohexane, and the results are found in the Table 1.

EXAMPLE 3

A 0.9Ir-0.1Cu/$Al_2O_3$ catalyst was prepared as in Example 1 with copper nitrate being added to the Ir solution. The catalyst was dried at 120° C. for 24 hr and reduced at 450° C. for 3 hr. The catalyst was used to ring open methylcyclohexane, and the results are found in the Table 1.

EXAMPLE 4

A 0.9Ir-1.0Cu/$Al_2O_3$ catalyst was prepared as in Example 1 with copper nitrate being added to the Ir solution. The catalyst was dried at 120° C. for 24 hr and reduced at 450° C. for 3 hr. The catalyst was used to ring open methylcyclohexane, and the results are found in Table 1.

TABLE 1

| Example | Catalyst | Conversion, Wt. % | $C_7$ Paraffin Yield, Wt. % | $C_1$ Yield, Wt. % | $C_7$ Paraffin Yield/$C_1$ Yield |
|---|---|---|---|---|---|
| 1 | 0.9 Ir | 58 | 30 | 4 | 8 |
| 2 | 0.9 Ir-0.03 Cu | 33 | 21 | 2 | 11 |
| 3 | 0.9 Ir-0.1 Cu | 20 | 13 | 1 | 15 |
| 4 | 0.9 Ir-1.0 Cu | 3 | 0 | 1 | — |

Examples 1–4 illustrate that the addition of Cu decreases the activity of the Ir catalyst. However, the influence of Cu on cracking to methane is substantial and decreases the formation of this undesirable product by about 50–75%. Furthermore, the selectivity to ring opened paraffins over Ir—Cu exceeds that of the exclusively Ir-containing catalysts by about 20–25%, and the ratio of the paraffin to methane selectivity represents a 50–90% increase for the Ir—Cu catalysts. The results further demonstrate that a critical balance is required between the Ir and Cu content of the catalyst as the 1.0 wt. % Cu catalyst is significantly deactivated.

EXAMPLE 5

A 0.9Ir-0.3Sn catalyst was prepared as in Example 1 by impregnating 50 g of alumina containing 0.3 wt. % Sn. The Sn-alumina was synthesized as described in U.S. Pat. No. 4,963,249. The catalyst was dried at 120° C. for 24 hr and reduced at 450° C. for 3 hr. The catalyst was then used to ring open methylcyclohexane under the following conditions: 300° C., 200 psig, 10 W/H/W, $H_2$/Oil=6. The results are detailed in Table 2.

TABLE 2

| Example | Catalyst | Conversion, Wt. % | $C_7$ Paraffin Yield, Wt. % | $C_1$ Yield, Wt. % | $C_7$ Paraffin Yield/$C_1$ Yield |
|---|---|---|---|---|---|
| 1 | 0.9 Ir | 58 | 30 | 4 | 8 |
| 5 | 0.9 Ir-0.3 Sn | 47 | 39 | 1 | 44 |

These data illustrate that given a comparable amount of conversion, the Ir—Sn catalyst has a higher yield of ring opened paraffins, while the methane yield is decreased by 75%. Thus, the Ir—Sn catalyst acquires an extremely favorable paraffin to methane selectivity benefit.

EXAMPLE 6

A 0.6Pt-0.6Ir catalyst was prepared as in Example 1, and used to ring open methylcyclohexane under the following conditions: 300° C., 800 psig, 10 W/H/W, $H_2$/Oil=6. The results are summarized in the Table 3.

EXAMPLE 7

A 0.6Pt-0.6Ir-0.1Sn catalyst was prepared as in Example 1, and then used to ring open methylcyclohexane. The results are summarized in the Table 3.

TABLE 3

| Example | Catalyst | Conversion, Wt. % | C$_7$ Paraffin Yield, Wt. % | C$_1$ Yield, Wt. % | C$_7$ Paraffin Yield/ C$_1$ Yield |
|---|---|---|---|---|---|
| 1 | 0.9 Ir | 61 | 53 | 0.9 | 58 |
| 6 | 0.6 Pt-0.6 Ir | 59 | 50 | 0.6 | 85 |
| 7 | 0.6 Pt-0.6 Ir-0.1 Sn | 49 | 43 | 0.4 | 111 |

Comparison of the catalysts of Examples 1 and 6 at approximately equivalent conversions show the Pt—Ir catalyst of Example 6 to be a more selective catalyst than the exclusively Ir-containing catalyst. The addition of Sn, Example 7, decreases activity modestly, but affords a significant increase in selectivity due to the suppression of cracking to methane, a benefit that is evident in the paraffin to methane selectivity value.

EXAMPLE 8

A 2.0Pt-0.3Sn catalyst was prepared with a process similar to Example 5, by impregnating 50 g of a 0.3 wt. % Sn containing alumina with 36 ml of a chloroplatinic acid stock solution, 28 mg, Pt/ml. The catalyst was dried at 120° C. for 24 hr and reduced at 450° C. for 3 hr. The catalyst was used to ring open methylcyclohexane under the following conditions: 350° C., 800 psig, 1 W/H/W, H$_2$/Oil=6. The results are shown in Table 4.

EXAMPLE 9

A 5.0Pt-0.3Sn catalyst was prepared with a process similar to Example 5, by impregnating 50 g of a 0.3 wt. % Sn containing alumina with 89 ml of a chloroplatinic acid stock solution, 28 mg, Pt/ml. The catalyst was dried at 120° C. for 24 hr and reduced at 450° C. for 3 hr. The catalyst was used to ring open methylcyclohexane under the following conditions: 350° C., 800 psig, 1 W/H/W, H$_2$/Oil=6. The results are found in the Table 4.

TABLE 4

| Example | Catalyst | Conversion, Wt. % | C$_7$ Paraffin Yield, Wt. % | C$_1$ Yield, Wt. % | C$_7$ Paraffin Yield/ C$_1$ Yield |
|---|---|---|---|---|---|
| 1 | 0.9 Ir | 61 | 53 | 0.9 | 58 |
| 8 | 2.0 Pt-0.3 Sn | 56 | 13 | 0.06 | 240 |
| 9 | 5.0 Pt-0.3 Sn | 61 | 14 | 0.02 | 769 |

The results demonstrate that at approximately equivalent conversion the Pt—Sn catalysts have low ring opening activity relative to the exclusively Ir-containing catalysts. However, the Pt—Sn catalysts also have exceptionally low cracking activity, which can be noted in an extremely favorable paraffin to methane selectivity. The bulk of the conversion over the Pt—Sn catalysts is ring isomerization.

EXAMPLE 10

The catalyst of Example 8 was used to ring open methylcyclohexane at high reaction temperatures than prior examples in order to increase the ring opening activity of the catalyst. The results are presented in Table 5.

EXAMPLE 11

The catalyst of Example 9 was used to ring open methylcyclohexane at high reaction temperatures to increase the ring opening activity of the catalyst. The results are presented in Table 5.

TABLE 5

| Example | Catalyst | R/O Temp, ° C. | Conversion, Wt. % | C$_7$ Paraffin Yield, Wt. % | C$_1$ Yield, Wt. % | C$_7$ Paraffin Yield/ C$_1$ Yield |
|---|---|---|---|---|---|---|
| 1 | 0.9 Ir | 300 | 61 | 53 | 0.9 | 58 |
| 8 | 2.0 Pt-0.3 Sn | 350 | 56 | 13 | 0.06 | 240 |
| 9 | 5.0 Pt-0.3 Sn | 350 | 61 | 14 | 0.02 | 769 |
| 10 | 2.0 Pt-0.3 Sn | 400 | 86 | 73 | 0.5 | 142 |
| 11 | 5.0 Pt-0.3 Sn | 400 | 78 | 65 | 0.2 | 280 |

Examples 10 and 11 illustrate that at high severity process conditions the catalysts of this invention achieve high ring opening activity while maintaining cracking to methane yields of less than that of the Ir-containing catalyst which operates at temperatures 100° C. cooler. The use and operation of the Ir-containing catalyst at the temperatures shown for the Pt—Sn catalysts leads to extensive cracking and methane yields in excess of 50 wt. %. The Pt—Sn catalysts are clearly capable of operation at high temperature conditions while retaining a high paraffin to methane ratio selectivity benefit.

Table 6 presents comparative data for the catalysts of the preceding Table 5 which show that catalysts of Examples 8–11 ring open methylcyclohexane to a lesser branched product than does the exclusively Ir-containing catalyst. This is reflected in the degree of tertiary bond cleavage leading to the formation of n-heptane as contrasted with the cleavage of non-tertiary bonds leading to the formation of isoheptanes.

TABLE 6

| Example | Catalyst | Tertiary Bond Cleavage, % |
|---|---|---|
| 1 | 0.9 Ir | 5 |
| 8 | 2.0 Pt-0.3 Sn | 18 |
| 9 | 5.0 Pt-0.3 Sn | 21 |
| 10 | 2.0 Pt-0.3 Sn | 12 |
| 11 | 5.0 Pt-0.3 Sn | 10 |

Having now fully described this invention, it will be appreciated by those skilled in the art that the invention can be performed within a wide range of parameters within what is claimed, without departing from the spirit and scope of the invention.

What is claimed is:

1. A naphthene ring opening catalyst comprising a Group VIII metal selected from Ir, Pt, Pd, Rh, Ru, and combinations thereof, in an amount effective to ring open a naphthene ring of a naphthene ring-containing compound, the metal being supported on a substrate comprising at least one of Cu, Ag, Au, Zn, Ge, Sn, Pb, and combinations thereof in an amount effective to moderate cracking of a naphthene ring-containing feed to form methane, wherein said substrate also contains an effective amount of at least one modifier selected from the group consisting of Cs, Mg, Ca, and Ba effective for improving selectivity to increased linear paraffin functionality from naphthene ring-containing compounds and reduce isomerization of linear paraffins to branched paraffins.

2. The naphthene ring opening catalyst of to claim 1, wherein the Group VIII metal is present in a range from about 0.01 to about 10.0 wt. %.

3. The naphthene ring opening catalyst of claim 1, wherein the substrate contains at least one refractory inorganic oxide selected from alumina, silica, zirconia, titania, chromia, zinc oxide, magnesia, thoria, boria, silica-alumina, silica-magnesia, chromia-alumina, alumina-boria, silica-zirconia.

4. The naphthene ring opening catalyst of claim 3, wherein the substrate contains alumina.

5. The naphthene ring opening catalyst of claim 3, wherein the substrate contains at least one of Cs, Mg, Ca, and Ba in an amount ranging from about 0.1 to about 50 wt. %, based on the weight of the catalyst.

6. The naphthene ring opening catalyst of claim 1, wherein the Group IB, IIB, and IVA metal is at least one of Cu, Ag, Au, Zn, Ge, Sn, and Pb in an amount ranging from about 0.01 to about 5.0 wt. %, based on the weight of the catalyst.

7. The naphthene ring opening catalyst of claim 1, wherein the Group VIII metal is a combination of Pt and Ir and the Group IB, IIB, and IVA metal is Sn.

8. The naphthene ring opening catalyst of claim 1, wherein the Group VIII metal is Ir and the Group IB, IIB, and IVA metal is Sn.

9. A process for opening naphthene rings of naphthene ring-containing compounds in a feed stream, comprising:
    providing a naphthene ring-containing feed stream; and
    contacting the naphthene ring-containing feed stream with a catalyst which comprises a Group VIII metal selected from Ir, Pt, Pd, Rh, Ru, and combinations thereof, in an amount effective to ring open a naphthene ring of a naphthene ring-containing compound, the metal being supported on a substrate comprising at least one of Cu, Ag, Au, Zn, Ge, Sn, Pb, and combinations thereof in an amount effective to moderate cracking of a naphthene ring-containing feed to form methane, wherein said substrate also contains an effective amount of at least one modifier selected from the group consisting of Cs, Mg, Ca, and Ba effective for improving selectivity to increased linear paraffin functionality from naphthene ring-containing compounds and reduce isomerization of linear paraffins to branched paraffins.

10. The process of claim 9, wherein the Group VIII metal is present in a range from about 0.01 to about 10.0 wt. %.

11. The process of claim 9, wherein the substrate contains at least one refractory inorganic oxide selected from alumina, silica, zirconia, titania, chromia, zinc oxide, magnesia, thoria, boria, silica-alumina, silica-magnesia, chromia-alumina, alumina-boria, silica-zirconia.

12. The process of claim 11, wherein the substrate contains alumina.

13. The process of claim 11, wherein the substrate contains at least one of Cs, Mg, Ca, and Ba in an amount ranging from about 0.1 to about 50 wt. %, based on the weight of the catalyst.

14. The process of claim 9, wherein the Group IB, IIB, and IVA metal is selected from Cu, Ag, Au, Zn, Ge, Sn, Pb and combinations thereof in an amount ranging from about 0.01 to about 5.0 wt. %, based on the weight of the catalyst.

15. The process of claim 9, wherein the Group VIII metal is a combination of Pt and Ir and the Group IB, IIB, and IVA metal is Sn.

16. The process of claim 9, wherein the Group VIII metal is Ir and the Group IB, IIB, and IVA metal is Sn.

17. The process of claim 9, wherein ring opening is carried out at a temperature of from about 150° C. to about 400° C., a total pressure from about 100 to about 3,000 psig, a liquid hourly space velocity from about 0.1 to about 10 V/V/Hr, a hydrogen treat gas rate from about 200 to about 10,000 standard cubic feet per barrel (SCF/B), and wherein the feed stream is a petroleum feed stream which has a boiling point ranging from about 175° C. to about 600° C.

18. The process of claim 7, further comprising recovering the ring opened product.

19. The process of claim 18, further comprising blending the ring opened product with a petroleum stream having a boiling point ranging from about 175° C. to about 600° C., wherein the blend has a cetane number of at least about 40.

20. The process of claim 9, wherein the petroleum feed stream is at least one of diesel fuel, jet fuel, heating oil, vacuum gas oil, and light cycle oil.

21. The process of claim 9, wherein the naphthene ring-containing feed stream has a sulfur content of less than about 10 ppm and contains less than about 20 wt. % total aromatic compounds.

* * * * *